United States Patent
Smyth et al.

(10) Patent No.: US 11,202,744 B2
(45) Date of Patent: *Dec. 21, 2021

(54) PACKAGED PERSONAL CLEANSING PRODUCT

(71) Applicant: The Procter & Gamble Company, Cincinnati, OH (US)

(72) Inventors: Kelsey Marie Smyth, Cincinnati, OH (US); Edward Dewey Smith, III, Mason, OH (US); Shawn David McConaughy, Cincinnati, OH (US); Nancy Lorincz Leppla, Loveland, OH (US)

(73) Assignee: The Procter and Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/862,666

(22) Filed: Apr. 30, 2020

(65) Prior Publication Data

US 2020/0253850 A1    Aug. 13, 2020

Related U.S. Application Data

(63) Continuation of application No. 15/435,546, filed on Feb. 17, 2017, now Pat. No. 10,675,231.

(51) Int. Cl.
*A61K 8/00* (2006.01)
*A61Q 13/00* (2006.01)
(Continued)

(52) U.S. Cl.
CPC ............. *A61K 8/442* (2013.01); *A61K 8/345* (2013.01); *A61K 8/463* (2013.01); *A61Q 13/00* (2013.01);
(Continued)

(58) Field of Classification Search
CPC ........ A61K 8/463; A61K 8/345; A61K 8/442; A61K 2800/87; A61Q 13/00; A61Q 19/10;
(Continued)

(56) References Cited

U.S. PATENT DOCUMENTS

| 2,438,091 A | 3/1948 | Lynch |
| 2,528,378 A | 10/1950 | Mccabe, Jr. |

(Continued)

FOREIGN PATENT DOCUMENTS

| CA | 2110951 A1 | 6/1994 |
| CA | 2196774 A1 | 2/1996 |

(Continued)

OTHER PUBLICATIONS

PLUS Search generated internally by the USPTO support staff for this application attached and requested by examiner using STIC internal services, Feb. 25, 2021 (Year: 2021).*

(Continued)

*Primary Examiner* — Vishal Pancholi
*Assistant Examiner* — Bob Zadeh
(74) *Attorney, Agent, or Firm* — John G. Powell; Alexandra S. Anoff; Carrie A. Morgan (57) ABSTRACT

A method of formulating a personal cleansing product that will adhere to skin, includes: combining a cleansing composition with from about 18% to about 70%, by weight of the composition, of a surfactant; wherein the composition has a low shear viscosity of 100 Pa*s or more and a high shear viscosity 5 Pa*s or less; and a package with an orifice, wherein the package has a dispensing velocity of 50 cm/s or more.

9 Claims, 2 Drawing Sheets

(51) Int. Cl.
| | |
|---|---|
| *B65D 35/24* | (2006.01) |
| *A61Q 19/10* | (2006.01) |
| *A61K 8/44* | (2006.01) |
| *B65B 3/04* | (2006.01) |
| *A61K 8/46* | (2006.01) |
| *A61K 8/34* | (2006.01) |

(52) U.S. Cl.
CPC ............ *A61Q 19/10* (2013.01); *B65B 3/04* (2013.01); *B65D 35/24* (2013.01); *A61K 2800/87* (2013.01)

(58) Field of Classification Search
CPC ...... B65B 3/04; B65D 35/24; B01J 2229/186; B01J 29/44; B01J 29/90; B01J 38/12; C07C 13/15; C07C 2529/44; C07C 5/373; Y02P 20/584
USPC ....... 222/92–107, 180–181.3, 206–215, 380, 222/422, 490–491, 494–497, 511, 518, 222/540, 544–545; 53/212; 510/119, 510/130, 158–159; 141/2, 5, 18
See application file for complete search history.

(56) References Cited

U.S. PATENT DOCUMENTS

| | | | |
|---|---|---|---|
| 2,658,072 A | 11/1953 | Kosmin | |
| 2,758,072 A | 8/1956 | Sutherland | |
| 3,962,150 A | 6/1976 | Viola | |
| 4,728,006 A * | 3/1988 | Drobish | B65D 47/2031 222/181.3 |
| 4,747,977 A | 5/1988 | Whitehead | |
| 4,997,641 A | 3/1991 | Hartnett et al. | |
| 5,057,241 A * | 10/1991 | Merritt | C11D 3/3765 510/428 |
| 5,104,646 A | 4/1992 | Bolich, Jr. | |
| 5,106,609 A | 4/1992 | Bolich, Jr. | |
| 5,106,613 A | 4/1992 | Hartnett et al. | |
| 5,252,555 A | 10/1993 | Dartnell et al. | |
| 5,308,526 A | 5/1994 | Dias | |
| 5,346,639 A | 9/1994 | Hatfield | |
| 5,374,614 A | 12/1994 | Behan | |
| 5,409,630 A | 4/1995 | Lysy et al. | |
| 5,415,857 A | 5/1995 | Robbins et al. | |
| 5,449,763 A | 9/1995 | Wulff | |
| 5,468,725 A | 11/1995 | Guenin et al. | |
| 5,507,970 A | 4/1996 | Ishikawa et al. | |
| 5,580,848 A | 12/1996 | Drapier | |
| 5,585,343 A | 12/1996 | Mcgee | |
| 5,597,792 A | 1/1997 | Klier | |
| 5,747,436 A | 5/1998 | Patel | |
| 5,804,538 A | 9/1998 | Wei | |
| 5,839,614 A | 11/1998 | Brown | |
| 5,977,036 A | 11/1999 | Guskey | |
| 6,048,834 A | 4/2000 | Drapier et al. | |
| 6,074,996 A | 6/2000 | Elliott | |
| 6,107,261 A | 8/2000 | Taylor | |
| 6,136,771 A | 10/2000 | Taylor et al. | |
| 6,204,230 B1 | 3/2001 | Taylor et al. | |
| 6,268,330 B1 | 7/2001 | Leonard et al. | |
| 6,271,187 B1 | 8/2001 | Hodge | |
| 6,303,109 B1 | 10/2001 | Foerster | |
| 6,329,331 B1 | 12/2001 | Aronson | |
| 6,358,906 B1 | 3/2002 | Ochs et al. | |
| 6,362,155 B1 | 3/2002 | Kinscherf | |
| 6,405,901 B1 | 6/2002 | Schantz | |
| 6,429,177 B1 | 8/2002 | Williams et al. | |
| 6,440,907 B1 | 8/2002 | Santora | |
| 6,491,933 B2 | 12/2002 | Lorenzi | |
| 6,806,249 B2 | 10/2004 | Yang et al. | |
| 6,936,578 B2 | 8/2005 | Cordellina | |
| 6,977,082 B2 | 12/2005 | Seitz, Jr. et al. | |
| 6,998,382 B2 | 2/2006 | Yang et al. | |
| 7,094,739 B2 | 8/2006 | Kessler et al. | |
| 7,115,535 B1 | 10/2006 | Smith, III et al. | |
| 7,132,468 B2 * | 11/2006 | Tepe | A61K 8/26 524/446 |
| 7,608,575 B2 | 10/2009 | Panandiker | |
| 7,704,932 B2 | 4/2010 | Evans et al. | |
| 7,874,466 B2 | 1/2011 | Mcconville | |
| 7,879,780 B2 | 2/2011 | Tsaur | |
| 7,884,061 B1 | 2/2011 | Hermanson | |
| 8,008,239 B2 | 8/2011 | Anantaneni et al. | |
| 8,114,826 B1 | 2/2012 | Hermanson et al. | |
| 8,207,100 B1 | 6/2012 | Hermanson | |
| 8,207,101 B1 | 6/2012 | Yang | |
| 8,236,747 B2 | 8/2012 | Holzhauer et al. | |
| 8,263,096 B2 | 9/2012 | Myers | |
| 8,408,432 B2 | 4/2013 | Delamare | |
| 8,461,099 B2 | 6/2013 | Fraser et al. | |
| 8,672,195 B2 * | 3/2014 | Py | B65D 47/205 222/494 |
| 8,697,622 B2 | 4/2014 | Man | |
| 8,840,871 B2 | 9/2014 | Wei et al. | |
| 8,899,449 B2 | 12/2014 | Daansen | |
| 8,937,102 B2 | 1/2015 | Hessel | |
| 9,254,498 B2 | 2/2016 | Daansen | |
| 9,271,908 B2 | 3/2016 | Allef | |
| 9,849,309 B2 | 12/2017 | Bouzeloc | |
| 10,675,231 B2 * | 6/2020 | Smyth | B65B 3/04 |
| 10,806,686 B2 | 10/2020 | Smyth | |
| 10,952,949 B2 | 3/2021 | Smith, III et al. | |
| 10,952,950 B2 | 3/2021 | Smith, III et al. | |
| 2001/0056049 A1 | 12/2001 | Aronson | |
| 2002/0034489 A1 | 3/2002 | Wiegland et al. | |
| 2003/0180246 A1 | 9/2003 | Frantz | |
| 2004/0074924 A1 | 4/2004 | Kuhn | |
| 2005/0019299 A1 | 1/2005 | Librizzi et al. | |
| 2005/0020468 A1 | 1/2005 | Frantz | |
| 2005/0042192 A1 * | 2/2005 | Evans | A61Q 5/06 424/70.11 |
| 2005/0250658 A1 | 11/2005 | Putman | |
| 2006/0035807 A1 | 2/2006 | Kasturi | |
| 2006/0078525 A1 | 4/2006 | Tomokuni | |
| 2006/0084589 A1 | 4/2006 | Vlad | |
| 2006/0183662 A1 | 8/2006 | Crotty | |
| 2007/0027050 A1 * | 2/2007 | Crotty | A61Q 5/02 510/130 |
| 2007/0093404 A1 | 4/2007 | Gross | |
| 2007/0110700 A1 | 5/2007 | Wells | |
| 2007/0114246 A1 | 5/2007 | Awbrey | |
| 2007/0289613 A1 | 12/2007 | Geary | |
| 2008/0003247 A1 | 1/2008 | Shick | |
| 2008/0032909 A1 | 2/2008 | De | |
| 2008/0118591 A1 | 5/2008 | Natsch | |
| 2008/0139434 A1 | 6/2008 | Basappa et al. | |
| 2008/0153929 A1 | 6/2008 | Miyahara | |
| 2009/0095775 A1 | 4/2009 | Domoy | |
| 2009/0155383 A1 | 6/2009 | Kitko et al. | |
| 2009/0221463 A1 | 9/2009 | Kitko et al. | |
| 2009/0312224 A1 | 12/2009 | Yang et al. | |
| 2010/0136175 A1 | 6/2010 | Skiff | |
| 2010/0285155 A1 | 11/2010 | Gilbard | |
| 2011/0152146 A1 * | 6/2011 | Denutte | C11D 3/50 510/119 |
| 2011/0152147 A1 * | 6/2011 | Smets | C11D 17/0039 510/119 |
| 2011/0212879 A1 | 9/2011 | Madden | |
| 2011/0268778 A1 * | 11/2011 | Dihora | A61K 8/11 424/401 |
| 2011/0269657 A1 * | 11/2011 | Dihora | C11D 3/001 510/119 |
| 2011/0269658 A1 * | 11/2011 | Dihora | C11D 3/505 510/119 |
| 2011/0280823 A1 | 11/2011 | Madden | |
| 2011/0281827 A1 * | 11/2011 | Tamarkin | A61P 17/00 514/152 |
| 2011/0287073 A1 | 11/2011 | Strauss et al. | |
| 2012/0015009 A9 | 1/2012 | Taylor | |
| 2012/0091218 A1 | 4/2012 | Mikkelsen et al. | |
| 2012/0114819 A1 | 5/2012 | Ragnarsson | |
| 2012/0208898 A1 | 8/2012 | Dong et al. | |

(56) References Cited

U.S. PATENT DOCUMENTS

| | | |
|---|---|---|
| 2012/0212879 A1 | 8/2012 | Li |
| 2012/0316095 A1* | 12/2012 | Wei .................. C11D 3/226 |
| | | 510/159 |
| 2013/0012601 A1 | 1/2013 | Hessel |
| 2013/0029932 A1 | 1/2013 | Kachi |
| 2013/0045306 A1 | 2/2013 | De |
| 2013/0053295 A1 | 2/2013 | Kinoshita et al. |
| 2013/0075430 A1 | 3/2013 | Ragnarsson |
| 2013/0230610 A1 | 9/2013 | Redmond et al. |
| 2013/0267451 A1 | 10/2013 | Hardy |
| 2014/0017386 A1 | 1/2014 | Ragnarsson |
| 2014/0162979 A1 | 6/2014 | Palla-venkata |
| 2014/0219946 A1 | 8/2014 | Hloucha |
| 2014/0263443 A1 | 9/2014 | Furusawa |
| 2014/0371128 A1 | 12/2014 | Hotz et al. |
| 2015/0057208 A1 | 2/2015 | Frantz |
| 2015/0203799 A1* | 7/2015 | Bettiol ................ C11D 3/2086 |
| | | 510/235 |
| 2015/0237905 A1 | 8/2015 | Ragnarsson |
| 2015/0272197 A1 | 10/2015 | Swain et al. |
| 2015/0298875 A1 | 10/2015 | Dagnelie |
| 2015/0322374 A1 | 11/2015 | Tchakalova |
| 2015/0359725 A1 | 12/2015 | Glenn, Jr. et al. |
| 2015/0359726 A1 | 12/2015 | Glenn, Jr. et al. |
| 2015/0359727 A1 | 12/2015 | Glenn, Jr. et al. |
| 2015/0359728 A1 | 12/2015 | Glenn, Jr. et al. |
| 2016/0128917 A1 | 5/2016 | Wei |
| 2016/0128927 A1* | 5/2016 | Wei .................. A61Q 19/10 |
| | | 510/130 |
| 2016/0143821 A1 | 5/2016 | Chang |
| 2016/0167864 A1 | 6/2016 | De Cleir |
| 2016/0309871 A1 | 10/2016 | Torres Rivera et al. |
| 2016/0310369 A1 | 10/2016 | Thompson et al. |
| 2016/0310370 A1 | 10/2016 | Zhao et al. |
| 2016/0310371 A1 | 10/2016 | Zhao et al. |
| 2016/0310372 A1 | 10/2016 | Glenn, Jr. et al. |
| 2016/0310375 A1 | 10/2016 | Torres Rivera et al. |
| 2016/0310376 A1 | 10/2016 | Torres Rivera et al. |
| 2016/0310377 A1 | 10/2016 | Torres Rivera et al. |
| 2016/0310386 A1* | 10/2016 | Smith, III .............. A61K 8/345 |
| 2016/0310387 A1 | 10/2016 | Smith, III et al. |
| 2016/0310388 A1 | 10/2016 | Smith, III et al. |
| 2016/0310389 A1 | 10/2016 | Thompson et al. |
| 2016/0310390 A1 | 10/2016 | Smith, III et al. |
| 2016/0310391 A1 | 10/2016 | Smith, III et al. |
| 2016/0310392 A1 | 10/2016 | Smith, III et al. |
| 2016/0310393 A1 | 10/2016 | Chang et al. |
| 2016/0310397 A1* | 10/2016 | Johnson ................ A45D 19/02 |
| 2016/0310402 A1 | 10/2016 | Zhao et al. |
| 2016/0354300 A1 | 12/2016 | Thompson et al. |
| 2016/0374932 A1 | 12/2016 | Song |
| 2017/0087068 A1 | 3/2017 | Callens |
| 2017/0165155 A1 | 6/2017 | Glenn, Jr. et al. |
| 2017/0165156 A1 | 6/2017 | Glenn, Jr. et al. |
| 2017/0165157 A1 | 6/2017 | Glenn, Jr. et al. |
| 2017/0165162 A1 | 6/2017 | Glenn, Jr. et al. |
| 2017/0165163 A1 | 6/2017 | Glenn, Jr. et al. |
| 2017/0165164 A1 | 6/2017 | Zhao et al. |
| 2017/0165165 A1 | 6/2017 | Zhao et al. |
| 2017/0165191 A1 | 6/2017 | Glenn, Jr. et al. |
| 2017/0174413 A1 | 6/2017 | Callens et al. |
| 2017/0246101 A1 | 8/2017 | Iwata |
| 2017/0278249 A1 | 9/2017 | Stofel et al. |
| 2017/0304172 A1 | 10/2017 | Chang et al. |
| 2017/0304184 A1 | 10/2017 | Glenn, Jr. et al. |
| 2017/0304185 A1 | 10/2017 | Glenn, Jr. et al. |
| 2017/0304186 A1 | 10/2017 | Glenn, Jr. et al. |
| 2018/0110688 A1 | 4/2018 | Torres Rivera et al. |
| 2018/0110689 A1 | 4/2018 | Torres Rivera et al. |
| 2018/0110690 A1 | 4/2018 | Torres Rivera et al. |
| 2018/0110691 A1 | 4/2018 | Torres Rivera et al. |
| 2018/0110692 A1 | 4/2018 | Torres Rivera et al. |
| 2018/0110693 A1 | 4/2018 | Renock et al. |
| 2018/0110694 A1 | 4/2018 | Renock et al. |
| 2018/0110695 A1 | 4/2018 | Thompson et al. |
| 2018/0110696 A1 | 4/2018 | Johnson et al. |
| 2018/0110697 A1 | 4/2018 | Smith, III |
| 2018/0110704 A1 | 4/2018 | Zhao et al. |
| 2018/0110707 A1 | 4/2018 | Zhao et al. |
| 2018/0110709 A1 | 4/2018 | Smyth |
| 2018/0110710 A1 | 4/2018 | Zhao et al. |
| 2018/0110714 A1 | 4/2018 | Glenn, Jr. et al. |
| 2018/0235861 A1 | 8/2018 | Smyth |
| 2018/0235862 A1* | 8/2018 | Smyth .................. A61K 8/345 |
| 2020/0253850 A1* | 8/2020 | Smyth .................. A61K 8/463 |
| 2021/0128434 A1 | 5/2021 | Smith, III et al. |
| 2021/0169763 A1 | 6/2021 | Smith, III et al. |

FOREIGN PATENT DOCUMENTS

| | | |
|---|---|---|
| CA | 2631077 C | 3/2015 |
| CN | 1252263 A | 5/2000 |
| CN | 101039651 A | 9/2007 |
| CN | 101193619 A | 6/2008 |
| CN | 102258440 A | 11/2011 |
| CN | 103893060 A | 7/2014 |
| DE | 4315396 A1 | 11/1994 |
| DE | 19624051 A1 | 12/1997 |
| EP | 0232153 A2 | 8/1987 |
| EP | 0316726 A2 | 5/1989 |
| EP | 0368146 A2 | 5/1990 |
| EP | 0743310 A1 | 11/1996 |
| EP | 0780464 A2 | 6/1997 |
| EP | 1714678 A1 | 10/2006 |
| EP | 1859777 A2 | 11/2007 |
| EP | 2042216 B1 | 9/2015 |
| FR | 2998476 A1 | 5/2014 |
| GB | 2223236 A | 4/1990 |
| GB | 2280682 A | 2/1995 |
| GB | 2284215 A | 5/1995 |
| GB | 2351979 A | 1/2001 |
| GB | 2371307 A | 7/2002 |
| JP | 9194877 A | 7/1997 |
| JP | H1018177 A | 1/1998 |
| JP | H1053795 A | 2/1998 |
| JP | 10182366 A | 7/1998 |
| JP | 2000212031 | 8/2000 |
| JP | 2001213762 A | 8/2001 |
| JP | 200445869 | 12/2004 |
| JP | 3644658 B2 | 5/2005 |
| JP | 2007320884 A | 12/2007 |
| JP | 2010138348 A | 6/2010 |
| JP | 2010150315 A | 7/2010 |
| JP | 2012001597 A | 1/2012 |
| JP | 4873586 B2 * | 2/2012 .......... C10M 135/18 |
| JP | 4915720 B2 | 2/2012 |
| JP | 4965869 B2 | 4/2012 |
| JP | 5465872 B2 | 1/2014 |
| WO | 9418946 A1 | 9/1994 |
| WO | 9616160 A1 | 5/1996 |
| WO | WO9612787 A1 | 5/1996 |
| WO | 9730688 A1 | 8/1997 |
| WO | 9748378 A1 | 12/1997 |
| WO | 9806817 A1 | 2/1998 |
| WO | WO200062755 A1 | 10/2000 |
| WO | WO0076460 A2 | 12/2000 |
| WO | WO0137658 A2 | 5/2001 |
| WO | 0142409 A1 | 6/2001 |
| WO | 02066589 A2 | 8/2002 |
| WO | 02092050 A2 | 11/2002 |
| WO | WO02097020 A2 | 12/2002 |
| WO | 2004045576 A1 | 6/2004 |
| WO | 2008110995 A2 | 9/2008 |
| WO | WO2010052070 A2 | 5/2010 |
| WO | WO2010052071 A2 | 5/2010 |
| WO | WO2010052147 A2 | 5/2010 |
| WO | WO2011049932 A1 | 4/2011 |
| WO | 2011094714 A1 | 8/2011 |
| WO | 2012055855 A1 | 5/2012 |
| WO | WO2013007473 A2 | 1/2013 |
| WO | WO2013163074 A1 | 10/2013 |
| WO | 2014090959 A1 | 6/2014 |
| WO | 2016026777 A1 | 2/2016 |
| WO | WO2016077114 A1 | 5/2016 |

(56) References Cited

FOREIGN PATENT DOCUMENTS

| WO | WO2016149166 A1 | 9/2016 |
| WO | 2016172405 A1 | 10/2016 |
| WO | 2016172468 A1 | 10/2016 |
| WO | 2016172475 A1 | 10/2016 |
| WO | 2016172478 A1 | 10/2016 |
| WO | WO2016172472 A1 | 10/2016 |
| WO | WO2016172482 A1 | 10/2016 |
| WO | 2018075749 A1 | 4/2018 |

OTHER PUBLICATIONS

STIC Search Report generated by the USPTO support staff for this application (Chen Haoyi) attached and requested by examiner, Feb. 25, 2021 (Year: 2021).*

International Search Report and Written Opinion of the International Searching Authority, PCT/US2018/017741, dated May 9, 2018, 12 pages.

All Office Actions, U.S. Appl. No. 15/135,627 (P&G Case No. 13805M).
All Office Actions, U.S. Appl. No. 15/135,648 (P&G Case No. 13806M).
All Office Actions, U.S. Appl. No. 15/135,687 (P&G Case No. 13815M).
All Office Actions, U.S. Appl. No. 15/135,697 (P&G Case No. 13816M).
All Office Actions, U.S. Appl. No. 15/299,722.
All Office Actions, U.S. Appl. No. 15/435,546.
All Office Actions, U.S. Appl. No. 15/787,832.
All Office Actions, U.S. Appl. No. 17/141,581.
All Office Actions, U.S. Appl. No. 17/176,404.
All Office Actions, U.S. Appl. No. 17/176,417.
Dow—Methocel Cellulose Ethers Technical Handbook, p. 1-32, Jun. 1997.
Dow—Personal Care Solutions, Cellulosic Thickeners Product Selection Guide, p. 1-2, Feb. 2015.
Oetter et al., Ringing Gels and their Fascinating Properties, Colloids and Surfaces, vol. 38, 1989, pp. 225-250.

* cited by examiner

PACKAGED PERSONAL CLEANSING PRODUCT

FIELD OF THE INVENTION

This application relates to packaged personal cleansing products with a package and a cleansing composition with surfactant, and methods relating thereto.

BACKGROUND OF THE INVENTION

A challenge faced by body wash users is that the liquid properties of the body wash composition which allow it to be easily dispensed from a package onto the hand or implement used for cleansing, also allow it to flow off the hands or implement, making it difficult to close the package and start lathering without the product falling onto the floor and being wasted. As such, there is a desire for an improved body wash which is less likely to fall from the intended surface and be lost down the drain.

SUMMARY OF THE INVENTION

A method of reducing the slip velocity of a cleansing product, includes: formulating a cleansing composition to include from about 18% to about 70%, by weight of the composition of a surfactant, wherein the composition has a low shear viscosity of 100 Pa*s or more and a high shear viscosity 18 Pa*s or less.

A method of formulating a personal cleansing product that will adhere to skin, includes: combining a cleansing composition with from about 18% to about 70%, by weight of the composition, of a surfactant; wherein the composition has a low shear viscosity of 100 Pa*s or more and a high shear viscosity 5 Pa*s or less; and a package with an orifice, wherein the package has a dispensing velocity of 50 cm/s or more.

These and other variations will be described in more detail below.

DETAILED DESCRIPTION OF THE INVENTION

As used herein, the following terms shall have the meaning specified thereafter:

"Cleansing composition" refers to a composition intended for topical application to the skin for cleansing.

"Concentrated" when used with reference to the composition, refers to a total surfactant level of 18% or more, by weight of the composition.

"Dispensing velocity" is the velocity to dispense a target dose of a composition from a package as measured by the Dispensing Velocity Method.

"High shear viscosity" is the viscosity measured at a shear rate of 10 1/sec in accordance with the Viscosity Method. The units are Pascal seconds, abbreviated as Pa*s.

"Hydric solvent" refers to a solvent that is neutral organic species that contains at least 2 hydroxyl groups and is not a hydrotrope.

"Hydrotrope" refers to a charged, amphiphilic solubility modifier. Hydrotropes are generally charged olefins especially an olefin sulfonate such as an aromatic sulfonate.

"Low shear viscosity" is the viscosity measured at a shear rate of 0.01 1/sec in accordance with the Viscosity Method. The units are Pascal seconds, abbreviated as Pa*s.

"Microemulsion" as used herein refers to a thermodynamically stable isotropic mixture of oil, surfactant, and water comprising an interior hydrophobic core, wherein the droplets have a diameter greater than about 10 nm.

"Rinse-off" means the intended product usage includes application to skin followed by rinsing and/or wiping the product from the skin within a few seconds to minutes of the application step. The product is generally applied and rinsed in the same usage event, for example, a shower.

"Target dose" refers to the amount of a cleansing composition which is needed to deliver about 1 gram of surfactant, which is the approximate amount needed to wash a body (for example, a cleansing composition with 20% by weight of surfactant would be 1 gram/0.20 or 5 g for a target dose).

Current body wash consumers are often frustrated when the body wash they dispense on their hand or an implement falls off of the target surface and goes down the drain resulting in the need to dispense more product. This problem results from a combination of factors including the rheology profile of the product, the mass of product dispensed, and the dispensing pattern on the target surface which is itself related to package features such as size, design, and amount and selection of the orifice including any valve or related feature at the exit point from the package.

Many micelle body washes have a relatively low (less than 100 Pa*s), low shear viscosity, providing insufficient resistance to flow off the target surface after dispensing. In addition, a conventional dose of body wash is about 10 grams, which provides considerable stress to encourage such flow. Resistance to flow from the target surface after dispensing can be provided by increasing low shear viscosity. This can be accomplished by adding structure through the use of a polymer, structured surfactant phase, or other means. Unfortunately, a typical target body wash dose of about 10 grams of composition dispensed onto an area of about 1 inch square can provide a shear stress in the hundreds of Pascals when the surface is turned vertically which often happens during a cleansing event. This stress can be more than a hundred-fold greater than the yield stress of the composition.

Furthermore, when a high (≥100 Pa*s), low shear viscosity is introduced by compositional means (like thickeners and/or structure) to minimize flow off the target surface, a composition can become difficult to dispense. For example, our research suggests consumers are only willing to squeeze a package using no more than about 5 kg of force (dispensing force). Increasing viscosity can result in an untenably long dispensing time utilizing a force at or below that level. To mitigate the high force, a package with a relatively large orifice can be used, for example, a circular orifice having a diameter of 4-10 mm or larger. While the large orifice may reduce the dispensing force and/or the amount of time to dispense the composition, at the same time it reduces the dispensing velocity of the composition and encourages the dose to be dispensed in a pile at a single location. This leads to a further disadvantage of conventional body wash dispensed from conventional packages; the dispensing event does little to distribute the compositions across the target surface.

The better a composition is distributed on the surface onto which it is dispensed, the more contact area it has with the surface. This increase in contact area results in a composition which more easily resists flow off the target surface, because the stress causing it to flow is approximately its mass divided by the contact area (multiplied by the gravitational constant). Low, low shear viscosity encourages high contact area during dispensing but provides little resistance to flow thereafter; whereas high, low shear viscosity can provide the (desirable) subsequent resistance, but the viscosity also resists spreading onto the surface to diffuse the stress. One solution is to have cleansing compositions which do not significantly flow from the surface onto which they are dispensed. This can result from a combination of elements related to the composition, its rheology and dosing properties from the package, particularly the dispensing velocity.

Figure 1:
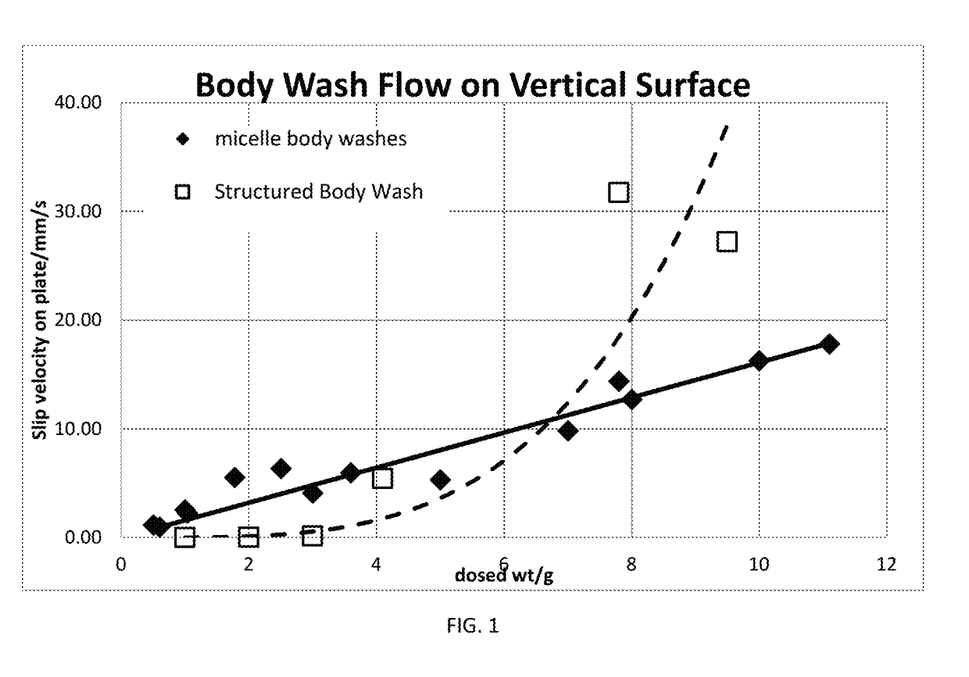
FIG. 1 is a graph of vertical slip on an aluminum sheet looking at slip velocity (mm/s) versus dose weight (g)

To achieve this result, typical body wash compositions were reviewed to determine their characteristics and establish the parameters of the problem to be solved. In a controlled test, body wash was dispensed in an evenly distributed straight line about 5 inches in length on a flat aluminum surface, the dispensed amount was weighed, and the surface was then turned vertically (the dosed amount in a line remaining parallel to the ground) to observe whether the composition flowed or remained stationary. The experiment was repeated multiple times with each composition to generate a response for a range of dispensed dose amounts both higher and lower than the target dose. If the composition flowed from the original horizontal line within about a minute, its average linear velocity was measured using a ruler and a stopwatch by returning the surface to a horizontal position after a measured time interval between about 5 to 120 seconds, and measuring the average distance the body wash traveled at its leading edge, divided by the time interval. This linear velocity when vertical was called the slip velocity. A sufficient number of trials were done with each body wash to establish a trend line (e.g., the regression lines in FIG. 1). From the trend line, the slip velocity of a composition at its target dose was expressed, using the regression line equation (either linear or power law as shown). When the slip velocity at the target dose of the composition is about 2 mm/s or less in this test, we find the composition adheres to the skin; and when the slip velocity is greater than about 2 mm/s, the composition is considered non-adhering (as noted in the examples, below). Adherence can be measured in accordance with the Composition Adhesion Method, below.

In line with the above, Comparative Compositions 1 and 2 with a low, low shear viscosity (represented with diamonds in FIG. 1), are dispensed, the compositions are non-adhering because of a high slip velocity. The stress is due, at least in part, to its high mass and it flows at a faster rate. It may move 15 mm every second at a standard 10 gram dose. Thus, these compositions can easily slip off of the target surface. Conversely, Comparative Examples 3, 4, and 5, which have a low shear viscosity of 1774 Pa*s, demonstrate little flow if dosed in a relatively small amount, less than about 4 grams (squares in FIG. 1). However, when dosed at a full amount needed to clean the body (a 10 g target dose), these same compositions also flow because of stress from the dispensed mass.

Thus, one way to combat too much flow is to reduce the target dose of the cleansing composition. In order to reduce the target dose of the cleansing composition, the composition can be concentrated. This means utilizing about 18% or more, by weight of the composition, of lathering surfactant. This reduces the target dose to about 5.6 grams or less, which has a much smaller mass, and therefore stress, and is much less likely to flow. Further concentration of the composition, will result in an even smaller dose, reduced stress, and reduced tendency to flow off of a target surface.

Because viscosity is the ratio of shear stress to shear rate (shear rate in turn relating directly to velocity), reducing shear stress by concentrating the composition has a direct effect on reducing slip velocity. Reducing the mass by reducing the dose, however, is generally insufficient by itself to make a composition adhere to a target surface without also optimizing its rheology and distribution on a surface. The composition can also be formulated and dispensed such that the composition can dispense a target dose without excessive force, distribute on the target surface so that the composition adheres, and subsequently resists falling off the target surface, reducing the likelihood the composition will flow too much. While increasing the viscosity will help, the ability to dispense the product from a package still needs to be considered with respect to the practical limit of a 5 kg force described above. If the viscosity is too high, the dispensing force can be too high to deliver a target dose or dispensing times can be too long to be useful if the force is maintained at or below a 5 kg dispensing force. For example, a consumer acceptable dispensing event would be a maximum of about 10 seconds, about 7 seconds, about 5 seconds, about 3 seconds, about 1 second, or about 0.5 seconds or less. Since dispensing is a high shear rate event, compositions that have a high shear viscosity that is too high can require significantly longer than this to dispense or require forces that are too high.

The rheology of a composition typically varies with shear rate, since Newtonian fluids, which have an invariant viscosity with shear rate, are uncommon with these compositions. Events that cause compositions to flow, such as dispensing, slip, and spreading can occur at different shear rates, so the viscosity profile as shear rate is varied, is important to understand and control in order to optimize its performance properties. In a rheometer, shear rate and other factors such as temperature can be controlled precisely for measurement purposes, whereas in real use conditions are less precise and shear rate can vary from one use to the next, and even exhibit a range of values within an event. Therefore we select shear rates for measurement and comparative purposes that are roughly representative of important behaviors.

Low shear rate performance which can be indicative of slip can be represented by the viscosity at 0.01 1/seconds. High shear rate performance, which can be indicative of behavior during dispensing at the package exit orifice, can be represented by the viscosity at 10 1/seconds. The Carreau equation is a model in which viscosity depends on the shear rate and is accurately descriptive of many body wash compositions. Fitting viscosity data to a Carreau viscosity model can be convenient in order to determine viscosity at a precise shear rate for comparative purposes from a data set generated by a scan that may or may not have produced a measurement at exactly the point of interest.

Figure 2:
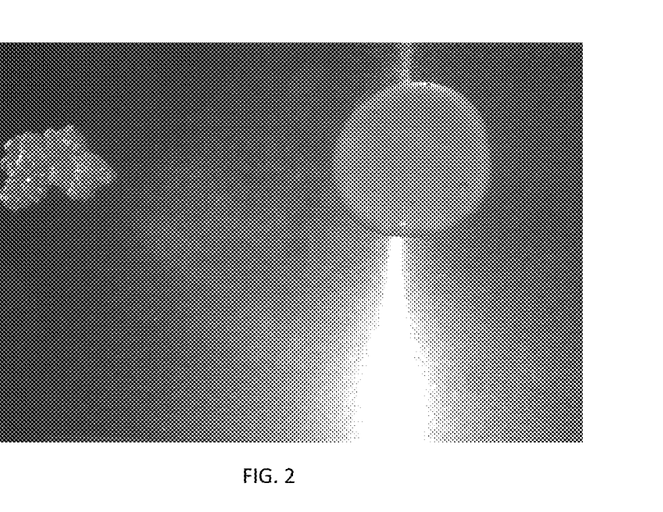
FIG. 2 is a picture of an inventive composition and a comparative composition after being dispensed on a horizontal aluminum sheet.
Figure 3:
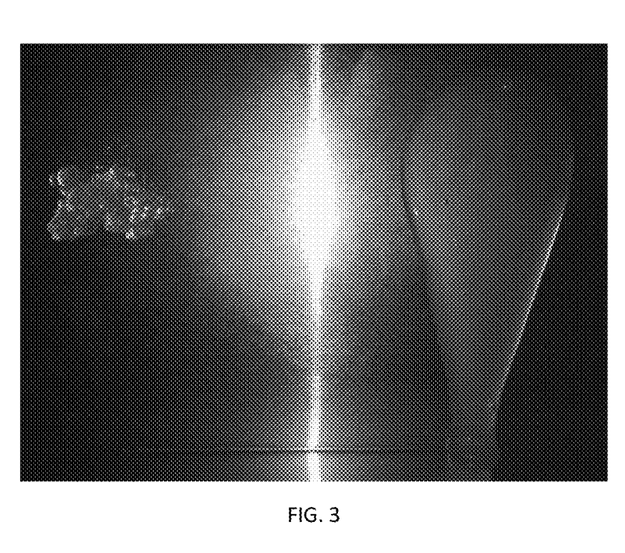
FIG. 3 is a picture of the compositions of FIG. 2, several seconds after the aluminum sheet has been turned to a vertical position.

As discussed above, a low viscosity at a lower shear rate, like one measured at 0.01 1/sec (Pa*s), can be indicative of a tendency to flow since static conditions on a flat surface involve either no or low shear. Thus, a higher viscosity at a lower shear rate is desired to combat compositional flow. For example, see FIGS. 2 and 3, where Inventive Example 6 is dispensed onto the left side of a horizontal aluminum plate and Comparative Example 2 is dispensed onto the right side of the plate, each at its approximate target dose. Inventive Example 6 has spread out somewhat during dispensing as it struck the plate, due to having a high dispensing velocity. Comparative Example 2 is on the right and is spreading in a pool under its own weight (not as a result of dispensed velocity). Inventive Example 6 has a low shear viscosity of 1127 Pa*s, while Comparative Example 2 has a low shear viscosity of 6.35 Pa*s. As you can see in FIG. 3, several seconds after the plate is turned vertical, Comparative Example 2 has flowed considerably, while Inventive Example 6 has slipped by less than 1 mm. In light of the above, a cleansing composition can have a low shear viscosity of about 100 Pa*s or more.

High shear viscosity can be indicative of compositions that will dispense without requiring too much force or too long of a dispensing time. Consumers prefer a composition that can be dispensed from a package with a force of about 5 kg or less. A cleansing composition can have a high shear viscosity of about 18 Pa*s or less allowing it to be dispensed in about 10 seconds or less using about 5 kg or less of force.

A sufficiently low viscosity for dispensing properties, yet a sufficiently high viscosity for adhering properties, is met by compositions that have a shear thinning viscosity profile within a specific range. Concentrated compositions having a low shear viscosity of about 100 Pa*s or more and a high shear viscosity of 18 Pa*s or less are able to be dispensed at a high velocity and can adhere to a target surface without flowing off the target surface. For example, concentrated compositions can have a low shear viscosity of about 150 Pa*s or more and a high shear viscosity of 15 Pa*s or less, a low shear viscosity of 200 Pa*s or more and a high shear viscosity of about 10 Pa*s or less, or a low shear viscosity of about 300 Pa*s or more and a high shear viscosity of about 5 Pa*s or less, when measured by the Viscosity Method.

In addition, the way a cleansing composition is dispensed can also impact whether it will flow too much based on how the composition is distributed on the target surface. The velocity at which a composition is dispensed can be important. Conventional liquid cleansing compositions are dispensed relatively quickly in a wide stream at a low velocity, with little means to direct the dispensed stream. For example, Comparative Example 1 is dispensed in only 1.1 seconds, but despite this short time its dispensing velocity is only 32.2 cm/s, because the width of the dispensed stream is a relatively wide 6 mm across (which is the fixed orifice dimension). As a result, the composition is generally dispensed into a mound on the target surface, inevitably contributing to the tendency to flow as a result of a large mass supported by a minimal contact area. Conversely, when a composition is dispensed at a high velocity, such as Inventive Example 9 at 272.3 cm/s, the package can be held further back from the target surface and the stream directed in a controlled manner onto the skin or other target, without requiring it to mound in only one spot, much like a garden hose spraying a stream can be directed much better than a bucket of water being dumped. As a result, at high velocity two advantages are observed. The first is a stream can be directed to more than one spot, for example directed in a line or a zig zag pattern, increases contact area which reduces the stress (i.e., force per area), which has benefits in reducing slip velocity as described above.

The second advantage is a composition with a high velocity upon impact with the target surface can spread out because of its momentum, increasing contact area with the surface, reducing stress, and therefore reducing the tendency to flow on the target surface. This provides a similar advantage in terms of reduced stress therefore reduced slip velocity, as shown in FIG. 4.

Figure 4:
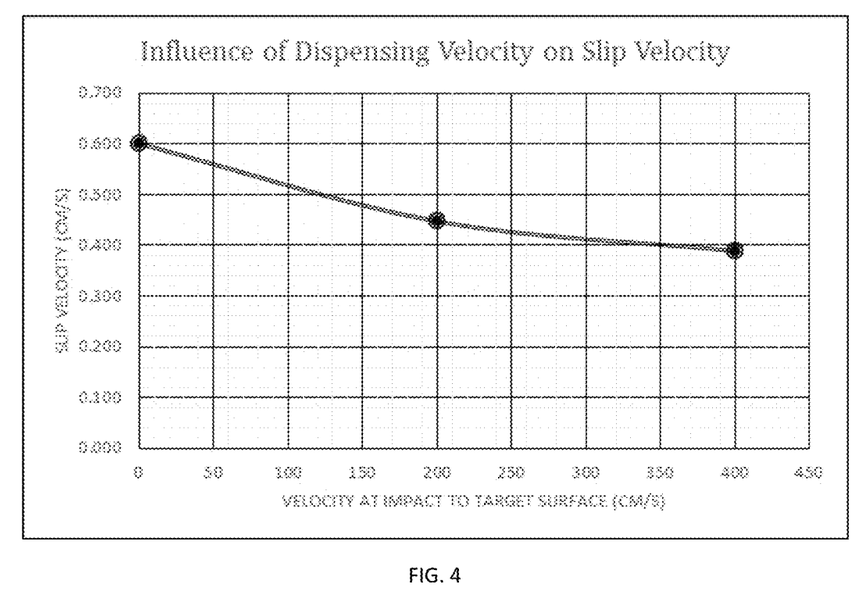
FIG. 4 is a graph of slip velocity (cm/s) versus velocity at impact of a target surface (cm/s).

FIG. 4 shows the composition of Inventive Example 12 tested in a simulated dispensing event where the composition was dispensed from a pipette at different heights between zero and 1 meter above a target surface (an aluminum plate) in order to control its impact velocity. When the composition impacted with the highest velocity, its subsequent slip velocity when the plate was turned vertically was the lowest, because the high impact velocity caused the composition to spread out more on the target surface.

The velocity at which a cleansing composition is dispensed is impacted by the package in which it is contained. Particularly, the ability to dispense a cleansing composition at a high dispensing velocity of 50 cm/s or more can provide adequate spreading of the cleansing composition upon contact with the target surface. Packages can be used which can have a fixed circular orifice. Fixed, circular orifices used to dispense body wash are generally smaller than 15 mm diameter, but utilizing a large fixed orifice can lead to a low dispensing velocity. Compositions of the current invention can be dispensed, for example, through packages containing a fixed orifice having a diameter of about 3.1 mm, 2.75 mm, 2.5 mm, 2 mm, 1.5 mm, 1.3 mm or about 1.1 mm or less. In addition, the fixed orifice may have a diameter of about 0.5 mm to about 3.1 mm; about 0.5 mm to about 2.75 mm, about 1.0 mm to about 2.5; about 1.0 mm to about 2.0 mm, about 1.0 mm to about 1.5 mm, or about 1.0 mm to about 1.3 mm. When a fixed orifice is non-circular, for example a star or wave, it can be mathematically represented by a circle having the same area, the circle having a diameter.

A package orifice may comprise a valve. The valve can be flexible and can open to different degrees during dispensing as a function of the fluid pressure that results from squeezing, so pressure can remain relatively high and a stream can be dispensed at a relatively high velocity as a result. Both a small fixed orifice, about 3.1 mm diameter or less, and an orifice with a valve can allow for the dispensing of a cleansing composition at an increased velocity. Flexible valves have advantages over fixed orifices because they can provide a more consistent velocity during a dispensing event due to the initial pressure required to open them at the onset of dispensing, and their ability to rapidly close to terminate dispensing, makes the dispensing event more controllable with less mess.

As for the utilization of a valve, some examples of suitable valves include valves made of flexible or elastomeric materials, for example polyurethane and silicone, although stiffer materials, like polyolefins, can also be used. The valves can consist of shapes cut into the flexible material, for example, a slit (i.e., line), cross or X-cut, V-cut, star, or snowflake design (which appears as an X-cut with an additional V-cut at the end of each line of the X). A slit valve may have one or more slits. During dispensing, the cuts open so that they essentially become the wetted perimeter of the valve when open. The elasticity of the valve can be adjusted by the material composition or by the valve thickness and other factors. Valve thickness can vary from, for example, about 0.025 inches thick to about 0.3 inches thick. A particularly suitable valve is an elastomeric silicone valve having an X-cut with 0.070 inches slit length and a height of about 0.121 inches manufactured by Aptar, Inc, Midland, Mich. USA under the trade name SimpliSqueeze® V21. In one example, a slit valve may have no slits with a length of more than 0.150 inches. The particulars of the valve make-up, like maximum opening size during dispensing, thickness of the valve material, and, for slit valves, the length and number of slits, can impact the dispensing ability of the package.

Packaged Personal Cleansing Product

In light of the above, it is believed an improved cleansing product can be provided where the product includes a package with a dispensing velocity of 50 cm/s or more and a cleansing composition with about 18% to about 70%, by weight of the composition, of surfactant; wherein the composition has a low shear viscosity of greater than or equal to 100 Pa*s and a high shear viscosity of less than or equal to 18 Pa*s. In addition, the dispensing velocity may be about 80 cm/s or more, about 100 cm/s or more, about 120 cm/s or more, about 150 cm/s or more, about 200 cm/s or more, or about 300 cm/s or more. The dispensing velocity may also be from 50 cm/s to about 1200 cm/s; from 80 cm/s to 1200 cm/s, from about 100 cm/s to about 1200 cm/s, from about 120 cm/s to about 1200 cm/s, from about 150 cm/s to about 1200 cm/s, or about 200 cm/s to about 1200 cm/s.

Cleansing Composition

In accordance with the above, a cleansing composition can comprise a surfactant, perfume, and water. Additionally, optional ingredients may also be included as noted herein, for example, a hydric solvent, preservatives, thickeners, hydrophobic oils, pH modifiers, additives, soap, etc. The cleansing composition is not in the form of a ringing gel. The cleansing composition can be in the form of a microemulsion or may contain a microemulsion phase. At least a portion of the cleansing composition may become a microemulsion upon dilution with water of about 2:1 or 3:1 by weight (water:composition) to about 10:1 by weight (water:composition).

A. Surfactant

A rinse-off cleansing composition includes a lathering surfactant. Surfactants can provide a cleaning benefit and lather properties to the compositions. The surfactant may be a single surfactant or a combination of multiple surfactants. In addition, a surfactant may be branched, linear, or a combination thereof. A composition may comprise from about 18% to about 70%, from about 20% to about 60%, from about 25% to about 60%, from about 25% to about 55%, from about 25% to about 50%, from about 28 to about 45%, from about 30% to about 60%, or from about 30% to about 45%, by weight of the composition, of total surfactant. The previous weight percentages of surfactant in the composition include primary surfactant and any cosurfactant.

The surfactant may be anionic, zwitterionic, amphoteric, nonionic, or a combination thereof. The surfactant may include a first surfactant and a cosurfactant. The rinse-off cleansing composition may include a first surfactant at a level of from about 16% to about 70%, from about 25% to about 60%, from about 35% to about 45%, from about 25% to about 45%, or from about 30% to about 40%, by weight of the composition. The first surfactant can be, for example, anionic.

The anionic surfactant can be linear or branched. The anionic surfactant may contain any counterion such as sodium, potassium, ammonium, triethanolamine, etc. The hydrocarbon chain can be an olefin or be branched or linear or cyclic, such as alkyl benzenes, and generally has between 10 and 20 carbons or 12 to 16 carbons. The anionic surfactant can comprise ethylene oxide groups, such as one EO, or two EO, or three EO, e.g., and can be a sulfate, sulfonate or carboxylate, including acidic sulfonates such as sulfosuccinates. Some exemplary anionic surfactants include a sulfate, an alkyl ether sulfate, an alkyl ether sulfate with about 0.5 to about 5 ethoxylate groups, sodium trideceth-2 sulfate, or a combination thereof.

Suitable anionic surfactants can include, for example, sodium trideceth sulfate and the sodium laureth sulfates. These materials can have varying levels of ethoxylation. Thus, the levels of ethoxylation are represented by an (n), for example, sodium trideceth-n sulfate. n can range from about 0.5 to about 5. Some exemplary anionic surfactants are sodium trideceth-2 sulfate, sodium trideceth-3 sulfate, sodium laureth-1 sulfate, sodium laureth-2 sulfate, sodium laureth-3 sulfate, or combinations thereof. The anionic surfactant can be a branched surfactant comprising sodium trideceth-2 sulfate, sodium trideceth-3 sulfate, or a combination thereof. In one example, the cleansing composition comprises from about 25% to about 45%, by weight of the composition, of sodium trideceth-2 sulfate.

The rinse-off cleansing composition may include from about 1% to about 20%, from about 2% to about 10%, from about 5% to about 10%, or from about 5% to about 8%, by weight of the composition, of a cosurfactant. The cosurfactant may be, for example, zwitterionic surfactant, amphoteric surfactant, nonionic surfactant, or a combination thereof. Suitable amphoteric or zwitterionic surfactants can include those described in U.S. Pat. Nos. 5,104,646 and 5,106,609.

Additional amphoteric detersive surfactants suitable for use in the rinse-off cleansing compositions can include those surfactants broadly described as derivatives of aliphatic secondary and tertiary amines in which an aliphatic radical can be straight or branched chain and wherein an aliphatic substituent can contain from about 8 to about 18 carbon atoms such that one carbon atom can contain an anionic water solubilizing group, e.g., carboxy, sulfonate, sulfate, phosphate, or phosphonate. Examples of compounds falling within this definition can be sodium 3-dodecyl-aminopropionate, sodium 3-dodecylaminopropane sulfonate, sodium lauryl sarcosinate, N-alkyltaurines such as the one prepared by reacting dodecylamine with sodium isethionate according to the teaching of U.S. Pat. No. 2,658,072, N-higher alkyl aspartic acids such as those produced according to the teaching of U.S. Pat. No. 2,438,091, and products described in U.S. Pat. No. 2,528,378. Other examples of amphoteric surfactants can include sodium lauroamphoacetate, sodium cocoamphoacetate, disodium lauroamphoacetate disodium cocodiamphoacetate, and mixtures thereof. Amphoacetates and diamphoacetates can also be used.

Zwitterionic surfactants suitable for use in the rinse-off cleansing compositions are well known in the art, and include those surfactants broadly described as derivatives of aliphatic quaternary ammonium, phosphonium, and sulfonium compounds, in which aliphatic radicals can be straight or branched chains, and wherein an aliphatic substituent can contain from about 8 to about 18 carbon atoms such that one carbon atom can contain an anionic group, e.g., carboxy, sulfonate, sulfate, phosphate, or phosphonate. Other zwitterionic surfactants can include a betaine, like an alkyl betaine or an alkyl amidopropyl betaine, like cocamidopropyl betaine. The composition may comprise a betaine, an alkyl amidopropyl betaine, a cocamidopropyl betaine, or a combination thereof.

Nonionic surfactants suitable for use can include those selected from the group consisting of alkyl ethoxylates, alkyl glucosides, polyglucosides (e.g., alkyl polyglucosides, decyl polyglucosides), polyhydroxy fatty acid amides, alkoxylated fatty acid esters, sucrose esters, amine oxides, or mixtures thereof. Some exemplary nonionic surfactants can include cocamide monoethanolamine, decyl glucoside, or a combination thereof.

B. Perfume

A rinse-off cleansing composition includes a perfume. A composition may comprise from about 0.25% to about 25%, from about 1% to about 30%, from about 2% to about 20%, from about 3% to about 15%, from about 4% to about 30%, from about 5% to about 25%, from about 6% to about 20%, from about 8% to about 15%, or from about 4% to about 15%, by weight of the composition, of perfume.

Perfume may include solvents such as triethyl citrate, isopropyl myristate, dipropylene glycol, or others, to help, for example, with the miscibility of the perfume molecules with each other or to reduce cost. Generally these perfume solvents provide minimal or negligible effects on surfactant compositions as a whole due to the low amount of perfume in the total composition and the amount of solvent in a perfume can be ignored. However, when solvent in the perfume accounts for more than about 5 wt % of the total hydric solvent in the cleansing composition, it should be accounted for. For example, when a perfume containing 10% hydric solvent is added to a cleansing composition at a level of 10 wt. % and the composition has 10 wt. % of added hydric solvent, the 1 wt. % of hydric solvent from the perfume accounts for a 9% increase in hydric solvent in the cleansing composition (1/11). Since this is more than a 5% change in the hydric solvent in the composition, it can be important. In this case, hydric solvent from the perfume is added (mathematically) to the hydric solvent from other sources added to the composition; and perfume is considered to comprise only the scented molecules and not the solvent, which is subtracted from the wt % perfume in the composition.

In addition, the weight ratio of perfume to surfactant can impact the ability of the composition to provide an enhanced fragrance benefit. Without being limited by theory, it is believed at least some of the perfume benefits, like bloom and residual scent are derived from an abundance of perfume on the basis of its relation to the surfactant due at least in part to the interaction of the perfume with surfactant as the composition is diluted. Perfume is soluble in surfactant micelles only to about 25% by weight of the surfactant. Above this level, the composition can become unstable unless steps are taken to form a phase to accept the abundance of perfume. However, forming those phases for stability of the perfume circles the composition back to where the perfume is bound within the composition and difficult to release. As such, a rinse-off cleansing composition comprises from about 0.5%, 1.0%, 2%, 4%, 5%, 8%, 10% 12%, 15%, 20%, 25%, 30% 35%, 40%, 50%, 70%, to about 15%, 30%, 40%, 50%, 60%, 70%, 90%, by weight of the surfactant, of perfume.

Perfumes generally contain a broad range of perfume raw materials having diverse properties. It is an oversimplification to suggest all of the perfume is in a particular location, like in the core of a microemulsion. The real picture is more complex, with perfume molecules in dynamic equilibrium and structures such as micelles and microemulsions can be percolating. Further, some perfume molecules may favor being among surfactant tails or even in the aqueous phase instead of the microemulsion core. In short, all perfume molecules within a perfume mixture do not behave identically. Certain generalizations are useful to explain observed behaviors without inferring that all molecules in a perfume behave identically. For our purposes, a broad array of perfume molecules in a perfume mixture is analyzed by averaging or summing their performance.

Certain perfume features may also impact perfume benefits, such as the proportion of perfume molecules within a volatility or molecular weight range. In general, Kovats Index (KI) is a useful parameter to differentiate perfume molecules. Perfume molecules having KI less than 1100 can be considered high blooming molecules; those having KI greater than 1400 can be considered high skin partitioning molecules; and those between (KI of 1100-1400) can be considered middle perfume notes which generally favor neither bloom nor skin partitioning, but contribute to some extent in both.

Perfume can be tailored to enhance features of the compositions. For example, while the compositions, including diluted compositions during use, can have a high activity coefficient, perfume molecules may selectively evaporate to enhance bloom or partition into the skin depending on their individual vapor pressure. It has surprisingly been discovered that the weight percentage of middle notes can impact the fragrance expression of the composition for the initial scent, for bloom and delivery on the skin. Particularly, better expression of the perfume is accomplished when the weight percentage of middle notes is restricted. For example, the composition may comprise a perfume, wherein the weight percentage of the perfume components having a Kovats Index of about 1100 to about 1700 comprises from about 0% to about 70%, from about 5% to about 50%, from about 5% to about 30%, or from about 5% to about 20%, by weight of the perfume.

In addition, it has also been discovered that the weight percentages of the perfume raw materials in a perfume composition can provide a strong rheological effect on the rinse-off cleansing composition. The wt % proportion of low, mid and high KI materials in the perfume impacts the elastic and viscous modulus of the composition as well as the viscosity. In general having a greater proportion of low KI materials results in a reduction in G' and G" and a lower tan delta (ratio of G"/G'). The following models of G' and G" were developed based on samples containing various proportions of low, mid and high KI materials and is a demonstration of the impact of KI on rheological properties for an exemplary concentrated body wash composition. G'=637.5−(1.118*wt % of Low KI Materials in a perfume)+(2.879*wt % proportion of Mid KI Materials in a perfume) and G"=7.510+(0.4056*wt % of Mid KI Materials in a perfume)+(0.6140*wt % of High KI materials in a perfume).

C. Water

A rinse-off cleansing composition includes water. Water may come in with other components or may be added as free water. A rinse-off cleansing composition may comprise from about 2% to about 75%, from about 5% to about 65%, from about 10% to about 60%, from about 15% to about 50%, or from about 25% to about 45%, by weight of the composition, of water.

In addition, the total weight percent of water and solvent can be important in a microemulsion composition since this defines the amount of solvent phase in which the microemulsion or surfactant structures are distributed. The total amount of solvent phase (approximately, the additive inverse generally of the surfactant level) is a key driver of surfactant phases due to proximity of surfactants. Thus, the composition may comprise from about 8% to about 85%, from about 15% to about 70%, from about 25% to about 65%, from about 30% to about 61%, by weight of the composition, of the combination of water and solvent.

Rheology

As discussed above, a cleansing composition can have a low shear viscosity of about 100 Pa*s or more. The cleansing composition can have a low shear viscosity of about 100 Pa*s to about 10,000 Pa*s, about 100 Pa*s to about 5,000 Pa*s, about 150 Pa*s to about 5,000 Pa*s, about 200 Pa*s to about 4,500 Pa*s, about 250 Pa*s to about 3,000, or about 250 Pa*s to about 1,200 Pa*s.

In addition, a cleansing composition can have a high shear viscosity of about 18 Pa*s or less. The cleansing composition can have a high shear viscosity of about 0.1 Pa*s to about 18 Pa*s, about 0.15 Pa*s to about 15 Pa*s, about 0.2 Pa*s to about 10 Pa*s, about 0.25 Pa*s to about 6 Pa*s, or about 0.25 Pa*s to about 5 Pa*s, about 0.15 Pa*s to about 4 Pa*s, about 0.2 Pa*s to about 3.5 Pa*s, about 0.25 Pa*s to about 3 Pa*s, or about 0.25 Pa*s to about 2.5 Pa*s.

D. Solvent

A rinse-off cleansing composition can include a solvent. The solvent can be used to modify the rheology properties or deliver other benefits such as enhanced perfume delivery or provide skin hydration benefits. A rinse-off cleansing composition may comprise from about 2% to about 30%, from about 2% to about 18%, from about 4% to about 16%, from about 5% to about 15%, or from about 7% to about 14%, by weight of the composition, of the solvent.

The solvent can be a hydric solvent. Examples of acceptable hydric solvents include dipropylene glycol (a glycol ether), diethylene glycol, dibutylene glycol, hexylene glycol, butylene glycol, pentylene glycol, heptylene glycol, propylene glycol, a polyethylene glycol having a weight average molecular weight below about 500, or a combination thereof. One example of a polyethylene glycol is PEG 300. Isomers are included in the generally descriptive solvents listed, for example, butylene glycol is meant to included 1,2-butanediol and 1,3-butanediol and 1,4-butanediol. When solvents are solid in the pure form (e.g., 1,6-hexanediol), they can be melted during the making process and are effective hydric solvents. The composition can comprise at least 5%, 6%, 8%, 10%, or 12%, to about 20%, 25%, 30%, 35%, or 40%, by weight of the composition, of hydric solvent.

In addition, a cleansing composition may comprise from about 2%, 5%, 7%, 10%, 12%, 20%, 25%, 30%, 40%, 50%, or 60%, to about 40%, 50%, or 60%, or any combination thereof, by weight of the surfactant, of hydric solvent. For example, one exemplary cleansing composition will have 6%, by weight of the composition, of hydric solvent, and 44.5%, by weight of the composition, of surfactant. Hydric solvent levels can be expressed as a percent of the surfactant because the solvent molecules can engage with the surfactant molecules.

An intermediate level of hydric solvent can be used to deliver both a combination of exemplary rheology and perfume delivery properties. Thus, the hydric solvent can be from about 15% to about 40%, from about 17% to about 35%, from about 20% to about 30%, expressed as a weight percent of the surfactant.

A solvent may also comprise a non-hydric solvent. Examples of non-hydric solvents include propylene carbonate, butanol, pentanol, hexanol, propylene glycol ethers, butyl butanoate, propyl propanoate, isopropyl propanoate, or a combination thereof. One example of a propylene glycol ether is propylene glycol monomethylether. One particular class of acceptable solvents is a glycol. The non-hydric solvent may comprise about 25%, 20%, 15%, 10% or 5% or less by weight of the solvent.

E. Preservatives

Liquid cleansing compositions often have a high water activity (i.e. about 0.95 or more), as measured by standard water activity meters such as a Rotonic Hygrometer. Water activity describes the availability of water within a composition to support various chemical and biological processes requiring water. Compositions with high water activity can allow growth of microorganisms and therefore generally utilize preservatives. For example, bacteria can grow at a water activity of about 0.90 or above and fungus can grow at a water activity of about 0.70 or above. Below these water activities, microorganisms generally dehydrate and die.

The rinse-off cleansing compositions as noted herein can have a low water activity, about 0.90 or less. This low water activity allows the compositions to naturally resist the growth of microorganisms and thus utilize minimal or even no, preservative. In addition, the use of high levels (5 wt. % or more) of glycols, like dipropylene glycol, can also help to prevent the growth of microorganisms and further support a composition which needs minimal or even no, preservative.

F. Hydrophobic Oils

The rinse-off cleansing composition may comprise a hydrophobic oil. Hydrophobic oil can help form a microemulsion phase due to low solubility in the palisade layer of micelles, to further enhance bloom and deposition on skin. The rinse-off cleansing composition may comprise from about 0% to about 25%, from about 2% to about 20%, or from about 3% to about 15% by weight of the composition, of a hydrophobic oil. Exemplary hydrophobic oils can include, for example, isopropyl myristate, isostearyl isostearate, behenyl behenate, triglycerides such as soybean oil, hydrocarbon such as mineral oil and petrolatum, or combinations thereof.

G. Additives

The rinse-off cleansing composition may comprise an additive. Additives are materials that are at least partially soluble in the perfume. It is believed that additives which are at least partially soluble in the perfume will also see a deposition benefit. Additives which are at least 5 wt %, or at least 10 wt %, or at least 20 wt % miscible with perfume may be employed to increase delivery of the additives to the skin or hair. Some examples of classes of material that can be soluble in the perfume are skin actives, vitamins, antibacterials, antifungals, chelants, hydrotropes, particles, or a combination thereof.

Examples of skin actives which can be included are sunscreens; anti-acne medicaments; antioxidants; skin soothing agents, skin healing agents; essential oils, skin sensates, anti-wrinkle medicaments, or mixtures thereof. Some examples of skin soothing agents can include, for example, aloe vera, allantoin, bisabolol, dipotassium glycyrrhizinate, or combinations thereof.

Examples of vitamins which can be included are Vitamin A (e.g., beta carotene, retinoic acid, retinol, retinoids, retinyl palmitate, retinyl proprionate, etc.), Vitamin B (e.g., niacin, niacinamide, riboflavin, pantothenic acid, etc.), Vitamin C (e.g., ascorbic acid, etc.), Vitamin D (e.g., ergosterol, ergocalciferol, cholecalciferol, etc.), Vitamin E (e.g., tocopherol acetate, tocopherol nicotinate, etc.), Vitamin K (e.g., phytonadione, menadione, phthiocol, etc.), or combinations thereof.

Examples of antibacterials and/or antifungals which can be included are glycolic acid, lactic acid, phytic acid, N-acetyl-L-cysteine, phenoxyethanol, phenoxypropanol, phenoxyisopropanol, zinc pyrithione, octopirox (piroctone olamine), climbazole, ketoconazole, thymol, terpineol, essential oils, or combinations thereof.

Examples of chelants which can be included are 2-aminoethyl phosphoric acid (AEP), N-phosphonomethyl aminodiacetic acid (PMIDA), 1-hydroxyethane-1,1-diphosphonic acid (HEDP), amino tris(methylene phosphonic acid) (ATMP), ethylenediamine tetra(methylene phosphonic acid) (EDTMP), diethylenetriamine penta(methylene phosphonic acid) (DTPMP), phytic acid, nitrilotrimethylene phosphonic acid (NIP), 2-hydroxypyridine oxide (HPNO), or combinations thereof.

The rinse-off cleansing composition may comprise from about 1% to about 20%, from about 2% to about 10%, or from about 3% to about 8%, by weight of the composition, of an additive.

H. Thickeners

The rinse-off cleansing composition may comprise from about 0.1% to about 4% by weight of the composition of a thickener. Preferred thickeners are hydrophilic such as cellulose derivatives, hydrophobically modified celluloses, starches and starch derivatives, polyacrylates including hydrophobically modified polyacrylates and polyacrylamides, bacterial polymers such as xanthan gum, tree and plant gums such as guar, insoluble thickeners such as cellulose.

I. Soap

Rinse-off cleansing compositions as described herein may also comprise soap.

Package for Personal Cleansing Composition

Cleansing compositions can be dispensed from a squeezable package with an orifice. The package can be a compact package, i.e., contain about 250 ml, or 200 ml, or 150 ml or less of volume to signal the contents are concentrated. The compositions can be dispensed from a package with a small fixed orifice. The size of the diameter of a small fixed orifice is about 3.1 mm or less and can be as small as about 0.5 mm.

The package may also contain a dispensing valve made from an elastomeric material having a cut, for example polyurethane and silicone, although stiffer materials can also be used. The size of the orifice may be large or small when using a valve. The valve may be a slit valve orifice or other flexible orifice. The size of a slit valve is specified by its maximum perimeter which is calculated from the dimensions and pattern cut into the material. The valve is generally closed when the package is not being used to dispense the composition, although it is also possible to cut a small hole or holes into the valve. Generally, the valve that is a slit (i.e., a line), or a V, or a cross shaped like a plus sign or the letter X, or it can include a V-shape added to the ends of the cross shaped cut which is called a snowflake cut. The cut can be any shape and there can even be more than one cut in the flexible material. When the cut is a slit, the perimeter is twice the slit length; when the cut is an X, the perimeter is four times the length of the cut, and so on. For example, the orifice can have a perimeter of from about 3 mm to about 30 mm, or 4 mm to 20 mm, or 5 mm to 15 mm.

During dispensing, the cut(s) open so that the cut(s) essentially becomes the wetted perimeter of the valve. The elasticity of the valve can be adjusted by the material composition or by the valve thickness, which can vary from about 0.025 inches thick to about 0.3 inches thick. A particularly suitable valve is an elastomeric silicone valve having an X-cut with 0.070 inches slit length and a height of about 0.121 inches manufactured by Aptar, Inc, Midland, Mich. USA under the trade name SimpliSqueeze® V21.

Methods of Use

Also included herein is a method of reducing the slip velocity of a cleansing product, comprising formulating a cleansing composition to include from about 18% to about 70%, by weight of the composition of a surfactant, wherein the composition has a low shear viscosity of 100 Pa*s or more and a high shear viscosity 18 Pa*s or less. The method may also include packaging the composition in a package comprising an orifice, wherein the package has a dispensing velocity of 50 cm/s or more.

A method for formulating a personal care composition that will adhere to skin is also included. This method may comprise combining a cleansing composition comprising from about 18% to about 70%, by weight of the composition, of a surfactant; wherein the composition has a low shear viscosity of 100 Pa*s or more and a high shear viscosity 5 Pa*s or less; and a package comprising an orifice, wherein the package has a dispensing velocity of 50 cm/s or more.

For the sake of brevity, all of the compositional and packaging components from above are not listed again here. It is envisioned, however, that such components can also be utilized in the methods of use just as if they were written again in this section.

Combinations

A. A packaged personal cleansing product, comprising: a. a squeezable package comprising an orifice, wherein the package has a dispensing velocity of 50 cm/s to 5000 cm/s; and b. a composition comprising from 18% to 70%, by weight of the composition, of surfactant; wherein the composition has a low shear viscosity of 100 Pa*s to 1200 Pa*s and a high shear viscosity of 0.1 Pa*s to 18 Pa*s.

B. The packaged personal cleansing product of paragraph A, wherein the package has a dispensing velocity of 80 cm/s to 1200 cm/s, 100 cm/s to 1200 cm/s, 120 cm/s to 1200 cm/s, from 150 cm/s to 1200 cm/s, or 200 cm/s to 1200 cm/s.

C. The packaged personal cleansing product of any of paragraph A or B, wherein the composition has a low shear viscosity of 150 Pa*s to 2,000 Pa*s, 200 Pa*s to 1,500 Pa*s, or 250 Pa*s to 1,200 Pa*s.

D. The packaged personal cleansing product of any of paragraphs A-C, wherein the composition has a high shear viscosity of 0.15 Pa*s to 15 Pa*s, 0.2 Pa*s to 10 Pa*s, 0.25 Pa*s to 6 Pa*s, 0.25 Pa*s to 5 Pa*s, 0.15 Pa*s to 4 Pa*s, 0.2 Pa*s to 3.5 Pa*s, 0.25 Pa*s to 3 Pa*s, or 0.25 Pa*s to 2.5 Pa*s.

E. The packaged personal cleansing product of any of paragraphs A-D, wherein the composition comprises from 20% to 60%, from 25% to 60%, from 25% to 55%, from 25% to 50%, from 28 to 45%, from 30% to 60%, or from 30% to 45%, by weight of the composition, of surfactant.

F. The packaged personal cleansing product of any of paragraphs A-E, wherein orifice is a fixed orifice with a diameter of 0.5 mm to 3.1 mm; 0.5 mm to 2.75 mm, 1.0 mm to 2.5; 1.0 mm to 2.0 mm, 1.0 mm to 1.5 mm, or 1.0 mm to 1.3 mm.

G. The packaged personal cleansing product of any of paragraphs A-F, wherein the orifice contains a valve.

H. The packaged personal cleansing product of paragraph G, wherein the valve is made of polyurethane or silicone.

I. The packaged personal cleansing product of any of paragraphs G-H, wherein the valve has a thickness of 0.025 inches to 0.3 inches.

J. The packaged personal cleansing product of any of paragraphs G-I, wherein the valve is a slit valve.

K. The packaged personal cleansing product of paragraph J, wherein the slit valve has one or more slits.

L. The packaged personal cleansing product of any of paragraphs J or K, wherein the slit valve has no slits with a length of more than 0.150 inches.

M. The packaged personal cleansing product of any of paragraphs J-L, wherein the slit valve has an X-shaped cut with a slit length of 0.070 inches and a height of 0.121 inches.
N. The packaged personal cleansing product of any of paragraphs A-M, wherein the surfactant comprises sodium trideceth-2 sulfate, cocamidopropyl betaine, sodium laureth-1 sulfate, or a combination thereof.
O. The packaged personal cleansing product of any of paragraphs A-N, wherein the composition further comprises a hydric solvent.
P. The packaged personal cleansing product of paragraph 0, wherein the composition comprises from 2% to 30%, from 2% to 18%, from 4% to 16%, from 5% to 15%, or from 7% to 14%, by weight of the composition, of the hydric solvent.
Q. The packaged personal cleansing product of any of paragraphs O-P, wherein the hydric solvent comprises a glycol.
R. The packaged personal cleansing product of paragraph Q, wherein the hydric solvent comprises dipropylene glycol, diethylene glycol, dibutylene glycol, hexylene glycol, butylene glycol, pentylene glycol, heptylene glycol, propylene glycol, a polyethylene glycol having a weight average molecular weight below about 500, or a combination thereof.
S. The packaged personal cleansing product of any of paragraphs O-R, wherein the hydric solvent comprises dipropylene glycol.
T. The packaged personal cleansing product of any of paragraphs A-S, wherein the composition further comprises from 0.25% to 25%, by weight of the composition, of perfume.
U. The packaged personal cleansing product of paragraph T, wherein the composition comprises from 1% to 30%, from 2% to 20%, from 3% to 15%, from 4% to 30%, from 5% to 25%, from 6% to 20%, from 8% to 15%, or from 4% to 15%, by weight of the composition, of perfume.
V. The packaged personal cleansing product of any of paragraphs A-U, wherein the composition further comprises a salt.
W. The packaged personal cleansing product of paragraph V, wherein the salt comprises sodium chloride.
X. The packaged personal cleansing product of any of paragraphs A-W, wherein the composition has a slip velocity of 0 mm/s to 2 mm/s, 0 mm/s to 1.5 mm/s, or 0 mm/s to 1.0 mm/s.
Y. The packaged personal cleansing product of any of paragraphs A-X, wherein the product adheres to dry skin.
Z. A method of reducing the slip velocity of a cleansing composition, comprising formulating the composition in accordance with any of paragraphs A-W and packaging it in a squeezable package with a dispensing velocity of 50 cm/s to 5000 cm/s.
AA. A method of formulating a personal cleansing product that will adhere to skin comprising combining a cleansing composition comprising from about 18% to about 70%, by weight of the composition, of a surfactant; wherein the composition has a low shear viscosity of 100 Pa*s or more and a high shear viscosity 5 Pa*s or less; and a package comprising an orifice, wherein the package has a dispensing velocity of 50 cm/s or more.
BB. The use of the packaged personal cleansing product of any of claims A-V for reducing the slip of a cleansing composition.
CC. The use of the packaged personal cleansing product of any of claims A-V for adhering the cleansing composition to the skin.

Examples

All inventive and comparative samples can be prepared by weighing the components together into a Speedmixer pot, stirring by hand briefly to homogenize the fluids, and then speedmixing for 60 seconds at 2750 rpm.

|  | Comparative Ex. 1 | Comparative Ex. 2 * | Comparative Ex. 3 |
| --- | --- | --- | --- |
| Commercial product name, in its commercial package | Old Spice Red Zone Swagger | Frozen Frosted Berry 3 in 1 Body Wash Shampoo Conditioner | Old Spice Dry Skin Defense Live Wire |
| sodium trideceth-2 sulfate |  |  | 16.6 |
| sodium laureth-3 sulfate | 6.5 |  |  |
| trideceth-3 |  |  | 2 |
| sodium lauryl sulfate | 2.5 |  |  |
| cocamidopropyl betaine | 1 |  | 4.9 |
| sodium chloride | 2 |  | 4.8 |
| citric acid | 0.25 |  | 0.35 |
| perfume | 1.25 |  | 1.4 |
| misc. preservative, color | 0.002 |  | 0.035 |
| sodium benzoate | 0.2 |  | 0.2 |
| water | QS |  | QS |
| tetrasodium EDTA | 0.1 |  | 0.15 |
| petrolatum |  |  | 15 |
| viscosity at 0.01 1/s (Pa-s) | 9.4 | 6.35 | 1774 |
| viscosity at 10 1/s (Pa-s) | 7.6 | 4.24 | 12.2 |
| package: | 16 fl oz | 3 fl oz | 16 fl oz |
| orifice diameter and type | 6 mm fixed | 4 mm fixed | 6 mm fixed |
| velocity (cm/s) | 32.2 | 13.8 | 28.4 |
| mass dispensing rate (g/s) | 9.1 | 1.7 | 8.3 |
| time to dispense dose (s) | 1.1 | 2.9 | 1.2 |
| maximum force (kg) | 3 | 5 | 5 |
| number of squeezes needed to dispense 1 dose | 1 | 2 | 1 |

-continued

|  | Comparative Ex. 1 | Comparative Ex. 2 * | Comparative Ex. 3 |
|---|---|---|---|
| Observation after dispensing | dispensing velocity too low | dispensing velocity too low | dispensing velocity too low |
| observations for adhesion test | non-adhering | non-adhering | non-adhering |

* Comparative Example 2 is a commercial micelle body wash having about 8% total solids and is marketed under the name 'Frozen' and contains the following ingredients: water, sodium laureth sulfate, cocamidopropyl Hydroxysultaine, Cocamidopropyl Betaine, PEG/PPG-18/18 Dimethicone, PEG-150 Distearate, PEG-80 Sorbitan Laurate, Polyquaternium-10, Glycol Distearate, Steareth-4, Fragrance, Citric Acid, Tetrasodium EDTA, Methylchloroisothiazoline, Methylisothiazolinone, Red 40

|  | Inventive Ex. 1 | Inventive Ex. 2 | Inventive Ex. 3 | Inventive Ex. 4 |
|---|---|---|---|---|
| sodium trideceth-2 sulfate | 37.9 | 19.3 | 57 | 36.07 |
| cocamidopropyl betaine | 5.88 | 2.9 |  | 6.21 |
| dipropylene glycol | 11.61 |  | 11 | 12.6 |
| sodium chloride |  | 2.9 |  |  |
| citric acid | 0.56 | 0.39 | 0.6 | 0.5 |
| perfume | 8 | 2.42 | 0.7 | 10 |
| misc. preservative, color |  |  |  | 0.034 |
| sodium benzoate |  |  |  | 0.25 |
| water | QS | QS | QS | QS |
| tetrasodium EDTA |  |  |  | 0.1 |
| viscosity at 0.01 1/s (Pa-s) | 664 | 864 | 249 | 1127 |
| viscosity at 10 1/s (Pa-s) | 1.82 | 4 | 4.48 | 2.3 |
| package: | 10 gram tube | 10 gram tube | 10 gram tube | 150 mL |
| orifice diameter and type | 1 mm fixed | 1 mm fixed | 1 mm fixed | 3.1 mm fixed |
| velocity (cm/s) | 194.33 | 62.24 | 57.96 | 90.8 |
| mass dispensing rate (g/s) | 1.526 | 0.489 | 0.455 | 6.85 |
| time to dispense dose (s) | 1.48 | 9.092 | 3.844 | 0.33 |
| maximum force (kg) | 5 | 5 | 5 | 2 |
| number of squeezes needed to dispense 1 dose | 1 | 1 | 1 | 1 |
| observations for adhesion test | adhering | adhering | adhering | adhering |

|  | Comparative Ex. 4 | Comparative Ex. 5 | Comparative Ex. 6 | Comparative Ex. 7 |
|---|---|---|---|---|
| Commercial product name | Old Spice Dry Skin Defense Live Wire | Old Spice Dry Skin Defense Live Wire |  |  |
| sodium trideceth-2 sulfate | 16.6 | 16.6 | 28.9 | 36.2 |
| trideceth-3 | 2 | 2 |  |  |
| cocamidopropyl betaine | 4.9 | 4.9 | 4.3 | 5.6448 |
| dipropylene glycol |  |  |  | 15.1456 |
| sodium chloride | 4.8 | 4.8 |  |  |
| glycerin |  |  | 22.8 |  |
| citric acid | 0.35 | 0.35 | 0.3 | 0.5376 |
| perfume | 1.4 | 1.4 | 9.1 | 7.68 |
| misc. preservative, color | 0.035 | 0.035 |  |  |
| sodium benzoate | 0.2 | 0.2 |  |  |
| water | QS | QS | QS | QS |
| tetrasodium EDTA | 0.15 | 0.15 |  |  |
| petrolatum | 15 | 15 |  |  |
| viscosity at 0.01 1/s (Pa-s) | 1774 | 1774 | 4825 | 21.1 |
| viscosity at 10 1/s (Pa-s) | 12.2 | 12.2 | 105 | 0.267 |
| package: | 150 mL | 1.9 fl oz | 1.9 fl oz | 1.9 fl oz |
| orifice diameter and type | Snowflake slit valve: Aptar V21-0.200SF | X-cut slit valve Aptar V21-070 | X-cut slit valve Aptar V21-070 | X-cut slit valve Aptar V21-070 |
| dispensing velocity (cm/s) | <10** | <10** | <10** | 280.7 |
| mass dispensing rate (g/s) | 4.3 | <0.2 | <0.5 | 1 |
| time to dispense dose (s) | 2.3 | >10 | >10 | 2.4 |
| maximum force (kg) | 5 | 5 | 5 | 5 |
| number of squeezes needed to dispense 1 dose | 1 | >5 | >4 | 1 |
| Observation after dispensing | Dispensing velocity too low | Dispensing velocity too low | Dispensing velocity too low; viscosity @ 10/s too high | Viscosity too thin |
| observations for adhesion test | Non-adhering | Non-adhering | adhering | Non-adhering |

**When dosing out of a variable valve, if the distance traveled by the dispensed product is less than 5 cm the velocity is recorded as less 10 cm/s

|  | Comparative Ex. 8 | Comparative Ex. 9 | Comparative Ex. 10 |
| --- | --- | --- | --- |
| sodium trideceth-2 sulfate | 59.3 | 53.62 | 56.63 |
| citric acid | 0.6 | 0.46 | 0.46 |
| perfume | 2 | 0.49 | 1.97 |
| water | QS | QS | QS |
| viscosity at 0.01 1/s (Pa-s) | 3,246 | 2,073 | 1,939 |
| viscosity at 10 1/s (Pa-s) | 8.21 | 5.22 | 4.43 |
| package: | 150 mL | 150 mL | 150 mL |
| orifice diameter and type | X-cut slit valve Aptar V21-145 | X-cut slit valve Aptar V21-070 | X-cut slit valve Aptar V21-070 |
| dispensing velocity (cm/s) | <10** | <10** | <10** |
| mass dispensing rate (g/s) | <1 | <1 | <1 |
| time to dispense dose (s) | 2 | 2.6 | >5 |
| maximum force (kg) | 5 | 5 | 5 |
| number of squeezes needed to dispense 1 dose | 2 | 1 | >2 |
| Observation after dispensing | Dispensing velocity too low | Dispensing velocity too low | Dispensing velocity too low |
| observations for adhesion test | adhering | adhering | adhering |

|  | Inventive Ex. 5 | Inventive Ex. 6 | Inventive Ex. 7 | Inventive Ex. 8 |
| --- | --- | --- | --- | --- |
| sodium trideceth-2 sulfate | 37.9 | 36.07 | 36.07 | 36.07 |
| cocamidopropyl betaine | 5.88 | 6.21 | 6.21 | 6.21 |
| dipropylene glycol | 11.61 | 12.6 | 12.6 | 12.6 |
| citric acid | 0.56 | 0.5 | 0.5 | 0.5 |
| perfume | 8 | 10 | 10 | 10 |
| misc. preservative, color |  | 0.034 | 0.034 | 0.034 |
| sodium benzoate |  | 0.25 | 0.25 | 0.25 |
| water | QS | QS | QS | QS |
| tetrasodium EDTA |  | 0.1 | 0.1 | 0.1 |
| viscosity at 0.01 1/s (Pa-s) | 664 | 1127 | 1127 | 1127 |
| viscosity at 10 1/s (Pa-s) | 1.82 | 2.3 | 2.3 | 2.3 |
| package: | 1.9 fl oz | 1.9 fl oz | 150 mL | 150 mL |
| orifice diameter and type | X-cut slit valve: Aptar V21-070 | X-cut slit valve: Aptar V21-070 | X-cut slit valve: Aptar V21-145 | X-cut slit valve: Aptar V25-145 |
| dispensing velocity (cm/s) | 191.6 | 276.4 | 137 | 201.1 |
| mass dispensing rate (g/s) | 1.2 | 2.2 | 3.5 | 4.6 |
| time to dispense dose (s) | 1.9 | 1 | 0.6 | 0.5 |
| maximum force (kg) | 5 | 5 | 2.5 | 3 |
| number of squeezes needed to dispense 1 dose | 1 | 1 | 1 | 1 |
| observations after dosing | adhering | adhering | adhering | adhering |

|  | Inventive Ex. 9 | Inventive Ex. 10 | Inventive Ex. 11 | Inventive Ex. 12 |
| --- | --- | --- | --- | --- |
| sodium trideceth-2 sulfate | 36.07 | 36.07 | 37.5 | 37.1 |
| cocamidopropyl betaine | 6.21 | 6.21 | 5.8212 | 5.7624 |
| dipropylene glycol | 12.6 | 12.6 | 12.4939 | 13.3778 |
| citric acid | 0.5 | 0.5 | 0.5544 | 0.5488 |
| perfume | 10 | 10 | 7.92 | 7.84 |
| misc. preservative, color | 0.034 | 0.034 |  |  |
| sodium benzoate | 0.25 | 0.25 |  |  |
| water | QS | QS | QS | QS |
| tetrasodium EDTA | 0.1 | 0.1 |  |  |
| viscosity at 0.01 1/s (Pa-s) | 1127 | 1127 | 652 | 439 |
| viscosity at 10 1/s (Pa-s) | 2.3 | 2.3 | 1.68 | 1.42 |
| package: | 150 mL | 150 mL | 1.9 fl oz | 1.9 fl oz |
| orifice diameter and type | X-cut slit valve: Aptar V21-070 | X-cut slit valve: Aptar V25-070 | X-cut slit valve: Aptar V21-070 | X-cut slit valve: Aptar V21-070 |
| dispensing velocity (cm/s) | 272.3 | 478.8 | 194.9 | 393.2 |
| mass dispensing rate (g/s) | 2.9 | 3.1 | 1 | 1.6 |

|  | Inventive Ex. 9 | Inventive Ex. 10 | Inventive Ex. 11 | Inventive Ex. 12 |
|---|---|---|---|---|
| time to dispense dose (s) | 0.8 | 0.7 | 2.4 | 1.4 |
| maximum force (kg) | 3.5 | 5 | 5 | 5 |
| number of squeezes needed to dispense 1 dose | 1 | 1 | 1 | 1 |
| observations after dosing | adhering | adhering | adhering | adhering |

|  | Inventive Ex. 13 | Inventive Ex. 14 | Inventive Ex. 15 | Inventive Ex. 16 |
|---|---|---|---|---|
| sodium trideceth-2 sulfate |  | 30.96 | 33.73 | 57 |
| sodium laureth-1 sulfate | 33.55 |  |  |  |
| cocamidopropyl betaine | 4.98 | 4.6 | 5.01 |  |
| dipropylene glycol | 11.73 |  |  | 11 |
| propylene glycol |  | 14.6 | 12.9 |  |
| citric acid | 0.42 | 0.38 | 0.42 | 0.6 |
| perfume | 16.75 | 14.6 | 12.9 | 0.7 |
| water | QS | QS | QS | QS |
| viscosity at 0.01 1/s (Pa-s) | 990 | 249 | 381 | 249 |
| viscosity at 10 1/s (Pa-s) | 1.89 | 0.95 | 1.38 | 4.48 |
| package: | 150 mL | 150 mL | 150 mL | 150 mL |
| orifice diameter and type | X-cut slit valve: Aptar V21-070 | X-cut slit valve: Aptar V21-070 | X-cut slit valve: Aptar V21-070 | X-cut slit valve: Aptar V21-070 |
| dispensing velocity (cm/s) | 311.2 | 284.6 | 107.1 | 125.84 |
| mass dispensing rate (g/s) | 1.37 | 1 | 0.595 | 1.157 |
| time to dispense dose (s) | 1.6 | 2.2 | 3.8 | 1.5 |
| maximum force (kg) | 5 | 5 | 5 | 5 |
| number of squeezes needed to dispense 1 dose | 1 | 1 | 1 | 1 |
| observations after dosing | adhering | adhering | adhering | adhering |

|  | Inventive Ex. 17 | Inventive Ex. 18 | Inventive Ex. 19 | Inventive Ex. 20 |
|---|---|---|---|---|
| sodium trideceth-2 sulfate | 19.3 | 19.51 | 17.94 | 17.94 |
| cocamidopropyl betaine | 2.9 | 2.89 | 2.66 | 2.66 |
| glycerin |  | 14.98 | 20.18 | 20.18 |
| citric acid | 0.39 | 0.22 | 0.2 | 0.2 |
| perfume | 2.42 | 14.98 | 7.37 | 7.37 |
| water | QS | QS | QS | QS |
| viscosity at 0.01 1/s (Pa-s) | 864 | 1540.4 | 3581.0 | 3581.0 |
| viscosity at 10 1/s (Pa-s) | 4 | 14.8 | 17.6 | 17.6 |
| package: | 150 mL | 150 mL | 150 mL | 150 mL |
| orifice diameter and type | X-cut slit valve: Aptar V21-070 | X-cut slit valve: Aptar V21-145 | X-cut slit valve: Aptar V21-145 | X-cut slit valve: Aptar V21-070 |
| dispensing velocity (cm/s) | 353.08 | 122.38 | 249.45 | 160.65 |
| mass dispensing rate (g/s) | 3.732 | 3.756 | 6.86 | 1.971 |
| time to dispense dose (s) | 1.2 | 1.2 | 0.7 | 2.5 |
| maximum force (kg) | 5 | 5 | 5 | 5 |
| number of squeezes needed to dispense 1 dose | 1 | 1 | 1 | 1 |
| observations after dosing | adhering | adhering | adhering | adhering |

Methods

Dispensing Velocity Method

1. Determine a target dose for the composition, which is the total dose (g of cleansing composition) required to cleanse, which generally utilizes 1 g active surfactant. A nominal dose for conventional body wash is 10 g.
2. Run the method at three compression speeds which are 2, 5 and 10 mm/s, each speed being a dispensing event.
    a. The dispensing velocity of a composition in a package can be determined following the steps below. A texture analyzer is used such as the TA.XTPlus (made by Texture Technologies). The instrument is set up on a lab bench or other hard surface having at least about 1 m of clear space on its side in order to dispense and observe the dispensed stream on the bench or other hard surface. A ¾ inch diameter ball probe is used to compress bottle packages and a 3.75 in. across flat plate is used to compress tube packages. The program is set up to run at a pre-test compression speed of 1 mm/s, various speeds (listed above) are used for the test speed, and the post-test speed is set to return to start at 50 mm/s to stop product from dispensing as soon as the test ends. The compression test is programmed to end when a maximum force of 5 kg is reached, where upon data collection is stopped. A 1 g trigger force is used to commence data collection. A package is filled completely to the top of the neck, leaving no air inside. To run a test tare a full package of product using a balance then lay it on its widest side on a platform, centered directly below the ball or plate probe with the cap open and the package pointed horizontally. The platform should be elevated at least 10 inches above the lab bench, the exact height is measured to the nearest quarter inch, from the center of the orifice to the lab bench surface. Next, the instrument probe squeezes the package until the programmed maximum force is reached, causing the composition to be horizontally dispensed. The weight dispensed is measured by weighing the package again using the balance after the dispensing event. Reprogram the instrument and repeat the test at each of the three compression speeds, refilling the package between the dispensing events so the package remains completely filled without air for each dispensing event. During any dispensing event, if an air pocket or air bubble is observed to disrupt flow, or is indicated by a sharp drop and recovery in the force-time instrument data curve which displays the real time results, the data are discarded and the measurement repeated after refilling the package. The time to dispense and the maximum force during the dispensing event are taken from the instrument data file or its graphical representation of the data.

b. Observe the weight dispensed for the three speeds. The observed weights should span a range that encompasses the target dose. If they do not, repeat the test using a faster or slower compression speed until the target dose is bracketed by the range of weights dispensed for all the dispensing events. The minimum compression speed that is used for the test is 0.25 mm/s and the maximum is 50 mm/s.

c. For a package containing a cap having a fixed orifice the velocity is determined by measuring the mass dispensing rate and the orifice area, as indicated below.

d. For a package having a variable orifice such as a valve, for example an elastomeric silicone valve, the test is run in the same manner and additional data are collected for the dispensed stream which are used to calculate velocity. During the test, the composition dispenses a stream which travels a horizontal distance, before landing on the lab bench. The maximum horizontal distance the product travels from the orifice outlet is measured using a yard stick.

3. Regress the weight dispensed in grams using the data from all dispensing events as a function of the compression speed using a linear regression (if the $r^2$ is greater than 0.95), or if the $r^2$ is lower, logarithmic, power, or exponential decay model (which ever model provides the highest $r^2$). Use the regression equation to calculate the compression speed which delivers a target dose. Note some products (for kids use, or travel size packages, e.g.) may not be able to deliver a sufficient dose in a single squeeze at these compression speeds. For these, proceed to determine the speed to deliver half of the target dose—the user would squeeze these packages twice if needed.

4. Regress the time to dispense in seconds using the data from all dispensing events as a function of the compression speed using a linear regression (if the $r^2$ is greater than 0.95), or if the $r^2$ is lower, logarithmic, power, or exponential decay model (which ever model provides the highest $r^2$). Use the regression equation to calculate the time to dispense which delivers a target dose, using the compression speed which delivers a target dose determined in the previous step.

a. The time to dispense which delivers a target dose should be greater than 0.3 sec. If it is not, repeat the entire procedure using a reduced maximum force because a consumer can't dose accurately at dispensing times lower than 0.3 sec, and discard any results using a maximum force that was unable to deliver a dose range span that includes the target dose. Reduce the maximum force by 0.5 kg (to 4.5 kg) and repeat the entire procedure. If the time to dispense which delivers a target dose remains less than 0.3 sec, reduce the maximum force again to 4 kg and repeat the entire procedure. Continue to reduce the maximum force in 0.5 kg increments and run the entire produce until the time to dispense the target is greater than 0.3 sec or a maximum force of 1.5 kg is required. If a maximum force of 1.5 kg is reached in the test without producing a time to dispense greater than 0.3 sec, that composition and package are incapable of delivering a target dose at a velocity that is acceptable.

5. Calculate the average mass dispensing rate (g/s) by dividing the target dose (g) by the time to dispense a target dose which was calculated.

6. If the dispensing orifice is fixed, such as for a plastic cap, determine the orifice area by measuring the orifice diameter with a digital caliper and calculating the area of a circle having the measured diameter. Express the result in square centimeters.

7. Determine the average density of the composition in g/cm$^3$. In many cases a nominal density of 1.0 g/cm$^3$ can be used for aqueous compositions.

8. If the package has a fixed orifice, calculate the dispensing velocity by dividing the average mass dispensing rate (g/s) by the density (g/cm$^3$) then again by the orifice area (cm$^2$). Express the resulting velocity in cm/s, which is the dispensing velocity.

9. If the package has a variable orifice (e.g., a flexible valve) use the platform height and horizontal distance the dispensed stream traveled measurements collected to calculate the dispensing velocities at each compression speed as follows. Calculate seconds to drop which is the square root of (the height (cm) divided by 490 cm/s) which is the amount of time the stream traveled before landing. The dispensing velocity at each compression rate is equal to the maximum horizontal distance the dispensed composition traveled before landing divided by the seconds to drop and is expressed in cm/s.

10. Next, for packages with variable orifice, regress the dispensing velocity results obtained at all compression speeds as a function of the compression speed using a linear regression (if the $r^2$ is equal to or greater than 0.95), or a logarithmic model if the linear regression has an $r^2$ below 0.95. Use the regression to calculate the velocity which delivers a target dose using the compression speed determined to deliver a target dose determined above which is the dispensing velocity.

Viscosity Method

Viscosity of a composition can be measured using a controlled stress rheometer such as a TA Instruments Model G2 with a 40 mm 1° cone at 25° C., or comparable instrument. The composition is loaded and trimmed and measured at shear rates between 0.005-500 l/seconds shear rate, in an equilibrium step ramp using 2 points per decade, 6 seconds sampling interval with 2 successive points within 2% viscosity value and a maximum time at each point of 36 seconds. Compositions that are very stiff may extrude from between the gap during the experiment in which case the test is halted and only the valid data are used. To generate data at higher shear rates for compositions that are too stiff to evaluate with this geometry, those compositions may be run using, for example, a capillary rheometer. Results are fit to a Carreau viscosity model by data analysis software provided with the instrument. Using the Carreau parameters obtained for a composition, its viscosity at 0.1 l/seconds and 10 l/seconds is determined from the Carreau equation as the low shear and high shear viscosity respectively, and is in units of Pascal seconds (Pa*s).

Composition Adhesion Method

To measure adhering properties, compositions are dispensed from their package onto a horizontal plate in a controlled manner and the surface is then turned vertically and observed for movement of the composition. A flat aluminum plate bent to a 90 degree angle is used, for example standard aluminum flashing. Composition is dispensed in a steady, even dose along a 5 inch line in a manner that the line remains horizontal when the panel is subsequently rotated to a vertical position. The target dose of a composition is determined by its concentration which is the dosed weight to deliver 1 gram of active surfactant as previously indicated. The panel is weighed while remaining flat, prior to and again after dosing to determine the dosed amount in grams. The dosing on the plate should deliver a consistent or even line of composition 5 inches in length. When it may be difficult to dose in an even line, dosing can begin away from the target 5 inch line by covering the area to both sides of the target 5 inch segment, commencing and ending dosing on the covered areas, so that the dosed 5 inch line is a relatively even line.

After weighing the dosed amount, the panel is turned to a vertical position allowing the line to be elevated but remaining horizontal, for a time period of between 5 to 120 seconds, using a stopwatch to measure elapsed time, and is returned to a horizontal position when the leading edge of the composition reaches the bottom of the vertical element. The panel is then returned to a flat horizontal position and the average rate of movement of the line of composition is measured using a ruler or digital calipers, in millimeters of movement per elapsed time. Compositions are held vertically for time intervals depending on their rate of movement. When compositions are not observed to move for 120 seconds, their rate of movement is said to be zero.

The test is repeated for enough trials with a composition and package to establish a trend for slip velocity as a function of the dosed amount which is typically about 10 trials at doses on both sides of the target dose. A suitable regression model is fit to the results and the slip velocity at the target dose is expressed, ensuring the model selected has no systematic bias (i.e., residual imbalance) in the region of the target dose. When the slip velocity at the target dose is 2 mm/s or less, the composition is said to be adhering. When the slip velocity at the target dose is greater than 2 mm/s, the composition is said to be non-adhering.

The linear rate of movement measured in this test is called the slip velocity, in units of mm/sec.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of reducing the slip velocity of a cleansing product, comprising:
    formulating a cleansing composition to include from about 18% to about 70%, by weight of the composition of a surfactant, wherein the composition has a low shear viscosity of 100 Pa*s or more and a high shear viscosity 18 Pa*s or less; wherein the slip velocity of the composition is 1.0 mm/s or less;
    packaging the composition in a package comprising an orifice, wherein the package has a dispensing velocity of 50 cm/s or more.

2. The method of claim 1, wherein the composition adheres to dry skin.

3. The method of claim 1, wherein the orifice is of a fixed size of 0.5 mm to 3.1 mm in diameter.

4. The method of claim 1, wherein the orifice is a fixed size of 0.5 mm in diameter to about 2.5 mm.

5. The method of claim 1, wherein the orifice comprises a slit valve.

6. The method of claim 5, wherein the slit valve has one or more slits.

7. The method of claim 5, wherein the slit valve has no slits with a length of more than 0.150 inches.

8. The method of claim 5, wherein the slit valve has a thickness of about 0.025 inches to about 0.3 inches.

9. The method of claim 1, wherein the package has a dispensing velocity of greater than 100 cm/s.

* * * * *